United States Patent [19]

Stern

[11] 4,282,435
[45] Aug. 4, 1981

[54] MONO-ENERGETIC NEUTRON VOID METER

[75] Inventor: Frank Stern, Burlington, Canada

[73] Assignee: Westinghouse Canada Limited, Hamilton, Canada

[21] Appl. No.: 30,478

[22] Filed: Apr. 16, 1979

[30] Foreign Application Priority Data

Aug. 22, 1978 [CA] Canada ................................ 309772

[51] Int. Cl.³ .............................................. G01T 3/00
[52] U.S. Cl. ..................................... 250/390; 250/391
[58] Field of Search ............... 250/258, 269, 308, 356, 250/357, 390, 391, 392; 73/17 A

[56] References Cited

U.S. PATENT DOCUMENTS

| | | | |
|---|---|---|---|
| 2,997,587 | 8/1961 | Mims | 250/390 |
| 3,100,395 | 8/1963 | Morley | 250/308 |
| 3,594,575 | 7/1971 | Shoemaker | 250/357 |
| 3,774,033 | 11/1973 | Scott et al. | 250/269 |

Primary Examiner—Alfred E. Smith
Assistant Examiner—Janice A. Howell
Attorney, Agent, or Firm—Robert H. Fox; Edward H. Oldham

[57] ABSTRACT

The ability to measure the ratio of vapor versus liquid in a nuclear steam generating system is highly desirable, particularly since, during transient events such as rapid depressurization, the vapor may not be in thermal equilibrium with its liquid and its distribution in the liquid may be highly non-uniform. By using a relatively mono-energetic neutron source such as Californium 252, exposing the medium under investigation to the radiation and using a proton recoil detector as an energy discriminating counter one can estimate the ratio of vapor to liquid by measuring the reduction of flux loss due to scattering when the medium includes vapor as well as liquid.

2 Claims, 1 Drawing Figure

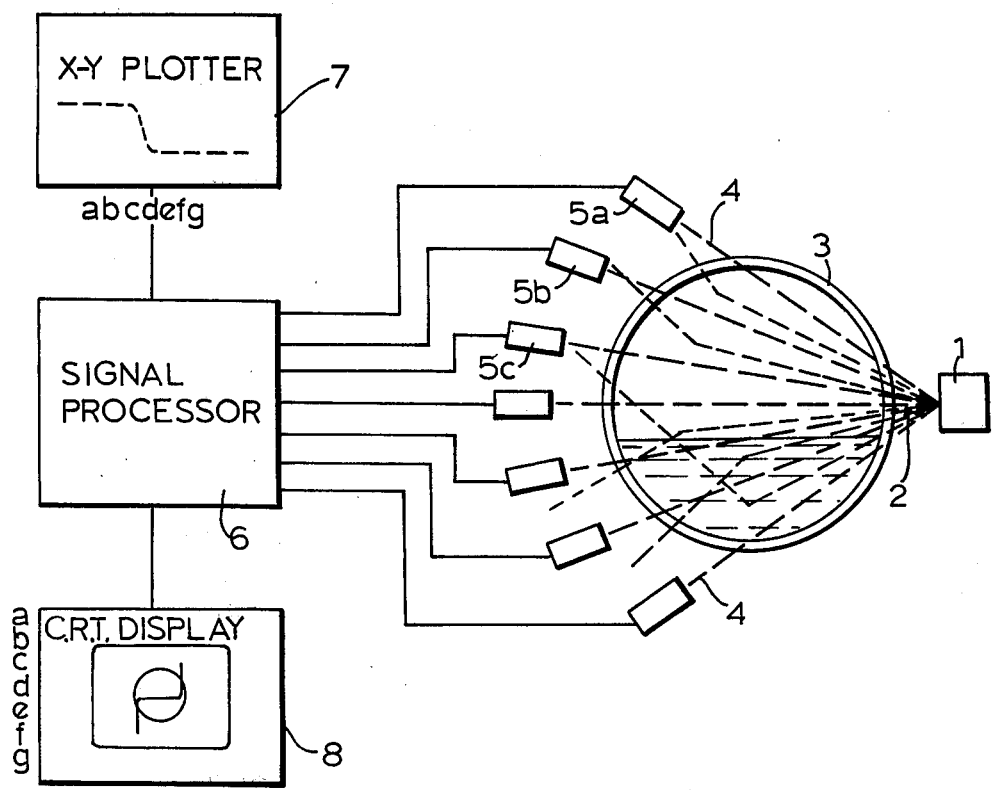

MONO-ENERGETIC NEUTRON VOID METER

In the production of steam, particularly in thermal nuclear power generating stations using water as a primary coolant, the ratio of steam to water in the mixture is of particular importance. During transient events such as rapid depressurization, the vapour may not be in thermal equilibrium with the liquid and its distribution in the liquid may be highly non-uniform. Since the rate of formation and distribution greatly affect coolant density, acceleration and flow impedance, the local ratio of steam to liquid and the steam distribution must be experimentally determined for both steady state and transient conditions.

Various methods have been proposed in the past to measure this vapour/liquid ratio. For example, a resistance probe can be used to measure the presence of liquid and vapour by virtue of the thermal conductivity difference. This method has several limitations, the most important being that a probe introduced into the flow perturbs the parameter being measured.

Another alternative is gamma ray scattering. A powerful gamma radiation source radiates energy through the mixed medium and measures the vapour/liquid ratio by measuring the level of loss of gamma flux due to scattering. This technique has a serious limitation referred to as "build-up factor" which reduces the sensitivity of the technique exponentially as the thickness of the medium in which the void is being measured increases. The "build-up factor" is due to rescattering of photons and the inability to discriminate between uncollided photons at the counter.

In order to overcome this limitation, it has been suggested that mono-energetic gamma radiation be used and a detector which rejects all photons of energy other than the energy source as the counter. Since scattering and rescattering changes the energy of the photons, this technique counts only uncollided flux.

The major limitation of this technique is in the very low energy available in the mono-energetic forms, making beryllium the only suitable material for containing the medium in which the void is being measured. As will be understood, introduction of beryllium into the system carries with it certain problems related to beryllium, such as its toxicity and brittleness. The low photon flux available from a mono-energetic source also precludes measurement of fast transients due to the counting time required.

A further alternative suggested has been to use neutrons from a nuclear reactor or other source. This eliminates the necessity of using beryllium since containment materials such as zirconium with good structural properties can be used and the high neutron scattering cross section of water provides a high degree of discrimination. However, this system also suffers from "build-up".

To overcome this problem, attempts have been made to measure only the collided flux, by placing counters around the pipe away from the collimated neutron beam. Since, with all liquid water in the pipe, most of the neutron flux is scattered, this results in a strong signal at the onset of boiling where methods counting uncollided flux see only a weak signal. However, as void fraction increases, the method rapidly loses sensitivity, and it cannot provide any information on the relative density distribution across the pipe, a factor of great importance in horizontal pipe runs.

In order to overcome the problems of the prior solutions, in accordance with this invention it is proposed to use mono-energetic neutrons to measure the steam/water ratio and measuring the radiation transmitted through the medium by means of proton recoil detectors which have very low sensitivity for thermal and near thermal neutrons. A suitable source of relatively mono-energetic epithermal neutrons is Californium 252. Any neutrons colliding with the nuclei of the medium in which the ratio is being determined would lose energy and would be rejected if rescattered into the counters.

The single FIGURE illustrates a simple system in accordance with this invention.

As will be seen, a source 1 contains a sample of Californium 252 which produces a radiation of epithermal neutrons symbolically indicated at 2. These neutrons pass into the medium under investigation which is contained in a conduit 3 which may be made of any suitable neutron transparent material such as zirconium which has good structural properties suitable for the purpose. The neutrons which pass unimpeded through the medium, schematically represented at 4, are counted by the proton recoil detectors 5a, 5b, 5c etc. The signal from each detector is passed to the signal processor 6 and represents the steam versus water content of the medium on the direct path from the source to the particular detector. It will be noticed that some of the neutrons are scattered by the water in the medium, and, if by chance, those which are scattered enter the counters they are rejected because of their different energy level after scattering.

The counters can be calibrated between the limits of no scattering as would occur in the absence of any liquid medium, i.e. pure steam and the other limit, complete liquid, i.e. no steam with maximum neutron scatter and at suitable points inbetween. The calibrated results can be displayed on the X-Y plotter 7 showing the medium density from one boundary of the conduit to the other or on a cathode ray tube 8 as a simulation of the steam water interface. In either case the signal processor scans the detector outputs sequentially synchronously with the "x" movement of the plotter or the "y" deflection of the cathode ray tube and the signal amplitude causes an amplitude related deflection of the display in the other axis.

The Y axis on the X-Y plotter 7 bears the designation abcdefg because the signals from detectors 5a, 5b etc. are displayed along the Y axis in sequence, with their amplitude displayed in the X axis. The plot can be smoothed out and represented as a continuous curve rather than a series of spikes by including a sample and hold circuit in signal processor 6.

Similarly, the cathode ray tube display presents a circle representing the pipe and the smoothed curve, produced by the signal processor, simulates the liquid level in the pipe.

Because of the high energy level of the neutrons, rapid counting is attained and fast transients can be detected and displayed.

What I claim is:

1. A method of measuring the steam/water ratio in a thermal generating system comprising:
    subjecting a cross section of the steam/water mixture to radiation consisting of mono-energetic epithermal neutrons;
    counting the number of neutrons which penetrate the medium without collision; and displaying the resultant count on means calibrated as the steam/water ratio of the medium subjected to radiation.

2. A method of measuring the steam/water ratio in a water cooled nuclear power steam generator comprising:
passing a portion of the steam/water medium through a zirconium conduit;
subjecting the conduit to radiation from Californium 252;
measuring the neutrons which penetrate the conduit and emerge therefrom;
rejecting those neutrons having an energy less than their original energy level; and
recording the quantity of neutrons measured in a plurality of locations and displaying the recorded quantities on means calibrated to represent the ratio of steam/water in the path terminating at each of said locations.

* * * * *